United States Patent [19]

Weetall

[11] 3,957,748

[45] May 18, 1976

[54] NICOTINAMIDE-ADENINE-DINUCLEOTIDE CHEMICALLY COUPLED TO WATER-INSOLUBLE CARRIERS

[75] Inventor: Howard H. Weetall, Elmira, N.Y.

[73] Assignee: Corning Glass Works, Corning, N.Y.

[22] Filed: July 30, 1971

[21] Appl. No.: 167,770

[52] U.S. Cl. .................................. 260/154; 195/63; 195/68; 195/103.5 R; 260/141; 260/142; 260/156

[51] Int. Cl.² .................... C07C 107/00; C07G 7/02

[58] Field of Search .......... 260/152, 154, 141, 142, 260/252; 195/63

[56] References Cited
UNITED STATES PATENTS

| | | | |
|---|---|---|---|
| 3,519,538 | 7/1970 | Messing et al. | 195/63 |
| 3,556,945 | 1/1971 | Messing | 195/63 |
| 3,574,062 | 4/1971 | Sato | 195/63 |

OTHER PUBLICATIONS

Sexton, "Chemical Constitution and Biological Activity", pp. 23–27 (1949).
Webb, "Enzymes", pp. 394–398 (1958).
Kay, Chemical Abstracts, Vol. 69, p. 7049 (1968).
Wilkinson, "Introduction to Diagnostic Enzymology", pp. 9–12 (1962).

*Primary Examiner*—Floyd D. Higel
*Attorney, Agent, or Firm*—James A. Giblin; Clinton S. Janes, Jr.; Clarence R. Patty, Jr.

[57] ABSTRACT

Nicotinamide-adenine-dinucleotide (NAD) can be coupled chemically to an essentially water-insoluble carrier material selected from the group consisting of glass particles having a diazotizable silane coupling agent attached thereto, p-aminobenzylcellulose, polyaminopolystyrene, and the half amide of benzidine-carboxymethylcellulose by diazotizing the carrier materials and reacting the diazotized materials with a solution of NAD. Methods of chemically coupling the NAD to such carriers are disclosed and the redox activity of NAD coupled to porous glass beads through an intermediate silane coupling agent is demonstrated.

6 Claims, 2 Drawing Figures

INVENTOR.
Howard H. Weetall
BY
James A. Giblin
ATTORNEY

NICOTINAMIDE-ADENINE-DINUCLEOTIDE CHEMICALLY COUPLED TO WATER-INSOLUBLE CARRIERS

BACKGROUND OF THE INVENTION

Field of the Invention

This invention relates to the preparation of water-insoluble composites of the coenzyme nicotinamide-adenine-dinucleotide (NAD) and various carrier materials. More specifically, the invention relates to methods of insolubilizing NAD in such a manner that the coenzyme can be used repeatedly in chemical reaction.

A coenzyme, sometimes referred to as a cofactor, is a thermostable nonprotein compound of relatively low molecular weight which is essential for the catalytic action of many enzymes. Enzymes are biological catalysts capable of initiating, promoting, and governing chemical reactions. All known enzymes are proteins and it is well known that they are essential for numerous biochemical reactions. Typically, an enzyme reacts with one or more substrates to produce products without being used up in the process or becoming a part of the products formed. In many enzymatic reactions, the presence of an active coenzyme is required. Examples of well known coenzymes are nicotinamide-adenine-dinucleotide (NAD), flavin-adenine-dinucleotide (FAD), and adenosine-triphosphate (ATP).

Nicotinamide-adenine-dinucleotide acts as a proton acceptor in its oxidized form (NAD) and as a proton donor in its reduced form (NADH). NAD and NADH have the following chemical structures:

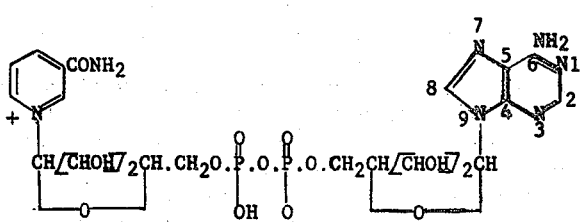

Coenzyme 1 (oxidized form) (NAD)

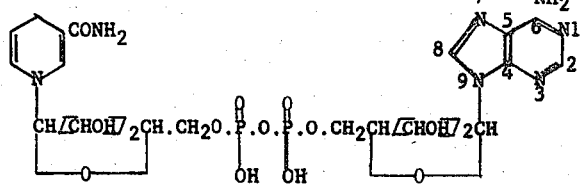

Coenzyme 1 (reduced form) (NADH)

NAD and other coenzymes are of great practical interest because of the essential roles they play in biochemical processes. For example, the interior of living cells is filled with many particulate structures, each having various functions to perform. One group of structures, the mitochondria, have as a primary function the oxidation of succinic acid and NADH and the coupling of those oxidations to the esterification of adenosine-diphosphate (ADT) to the triphosphate (ATP). Also, four of the five oxidation steps involved in the combustion of pyruvate to carbon dioxide and water consist of dehydrogenation in which hydrogen is transferred from the substrate to the oxidized coenzyme, NAD. The NADH so formed is reoxidized by a flavoprotein enzyme system in yet another biochemical reaction. Thus, it can be readily appreciated that NAD, with other coenzymes, are essential compounds in life processes. Consequently, considerable attention has been directed toward further understanding the roles coenzymes play in biological systems.

Because many enzyme systems require the presence of NAD or NADH, there are many present and potential applications in research, analytical procedures, and industry in which the coenzyme is and can be utilized. For example, it is known that many enzymes utilizing NAD exhibit reasonable binding constants for the nucleotide. Consequently, enzyme purification techniques would be possible if there were methods available for retaining the coenzyme in a column through which solutions known to contain certain enzymes could flow. Further, since the coenzyme is spectrophotometrically detectable, it can be used for the quantitative and qualitative analysis of various products in enzymatic reactions which require NAD or NADH since the coenzyme is commonly either oxidized or reduced in direct proportion to the amount of product produced or the amount of substrate transformed. Also, metabolic pathways may be constructed if there were methods for modifying the coenzyme in such a way that it could be made either water-insoluble or retainable within membranes without loss of its redox properties. The above applications are but a few of the many present and potential applications in which NAD is and will be essential.

There are, however, certain disadvantages accompanying the use of NAD which greatly limit its present and potential value as a research and industrial tool. For example, in many enzymatic reactions, the cost of the coenzyme exceeds the cost of the enzyme. Although some enzymes can be recovered for repeated use, the coenzyme is difficult to recover. Consequently, the more costly NAD can generally be utilized only once. Also, even though NAD is relatively stable in pure form, it is frequently rendered unstable or inactive by the presence of the other compounds with which it may be stored or used. Thus, further industrial uses of enzymatic reactions requiring NAD are limited by the high cost, unreusability, and the frequent instability of NAD.

Prior Art

Recently, there have been devised methods for rendering otherwise soluble enzymes water-insoluble by attachment to water-insoluble carriers in such a manner that the enzymes retain their catalytic power. For example, U.S. Pat. No. 3,519,538 teaches methods for chemically coupling enzymes to inorganic carriers in such a way that the enzymes remain catalytically active so they can be used repeatedly. Also, U.S. Pat. No. 3,556,945 teaches methods for absorbing enzymes to inorganic carriers such as glass particles. There has also been recently disclosed a method for stabilizing reduced NAD (NADH) by combining it with SH-group containing compounds. See Canadian Patent No. 862,061. In that disclosure, however, the reduced NAD is not rendered water-insoluble for repeated use but, rather, it is stabilized to the extent that it does not lose its activity when in contact with other compounds. Thus, even though the costly reduced form of NAD can be utilized more efficiently according to the above teaching, and even though it is known that NAD can be made more efficiently (see, for example, Canadian Pat. No. 868,877), the coenzyme can generally be used only once without further elaborate recovery procedures.

To date, there have been no known methods for overcoming the disadvantages associated with the coenzyme. Thus, there has been a continuing need for methods of modifying NAD in such a manner that the coenzyme is made water-soluble for repeated, economical use and stabilized in a biologically active form. The present invention, quite surprisingly, serves that need.

SUMMARY OF THE INVENTION

It has now been found possible to insolubilize the coenzyme NAD by chemically coupling it to an essentially water-insoluble carrier in such a manner that the coenzyme retains its redox properties. In a preferred embodiment, the NAD is coupled to a variety of diazotized organic and inorganic carriers by means of an azo linkage to form an insoluble, biochemically active composite. The composites can be easily removed from a reaction and used repeatedly in either the oxidized or reduced form. The redox activity of the coupled NAD is demonstrated indirectly by means of two experiments showing the presence of products which could have been formed only in the presence of active NAD.

SPECIFIC EMBODIMENTS

Figure 1:
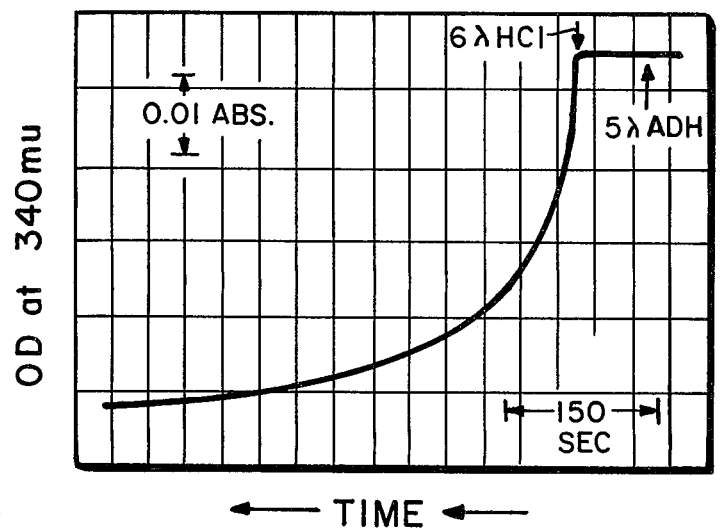
FIG. 1 is a plot showing a decrease in NADH with time which occurs in the presence of acetaldehyde and alcohol dehydrogenase after a sudden change in pH from 8.5 to 6.5.

NAD can be insolubilized by chemical coupling to a wide variety of essentially water-insoluble carriers. The carriers may be organic or inorganic. Among the organic carriers are diazotizable derivatives of cellulose such as p-aminobenzylcellulose, the half amide of benzidine-carboxymethylcellulose and polymers such as polyaminopolystyrene. Among the inorganic carriers that can be used to couple the coenzymes are those inorganic substances having available hydroxyl or oxide groups capable of coupling with silane coupling agents which can then be diazotized. The inorganic carriers may be either weak acids or weak bases. They may also be classified in terms of chemical composition as siliceous materials or non-siliceous metal oxides such as alumina, nickel oxide, and hydroxyapatite. Of the siliceous materials such as silica, silica gel, bentonite, wollastonite, and glass, a preferred carrier is glass, either in bead or porous form. The porous glass may be either particulate or in the form of an integral piece such as a disc.

Glass has the advantage in that it is dimensionally stable and it can be thoroughly cleaned to remove contaminants by such techniques as acid bathing or sterilization. Porous glass found useful as a carrier is readily available from Corning Glass Works as Code 7930 porous glass. Such porous glass can be prepared having various pore dimensions in accordance with the teachings of U.S. Pat. No. 2,106,744, U.S. Pat. No. 3,485,687, and U.S. Pat. No. 3,549,524.

Generally, the only requirements for the carriers are that, if organic, they can be modified for the coupling procedures disclosed below, and, if inorganic, they should have available oxide or hydroxyl groups for coupling with the silicon portion if the silane coupling agents.

The silane coupling agents are molecules which possess two different kinds of reactivity. They are organofunctional and silicon-functional silicon compounds characterized in that the silicon portion has an affinity for inorganic materials having available oxide or hydroxyl groups. The organic portion of the silane coupling agent can be tailored to combine with many organic compounds. The main function of the silane coupling agent is to chemically link the coenzyme (organic) to the carrier (inorganic). For examples of various silane coupling agents that have been used to couple enzymes to inorganic carriers, see U.S. Pat. No. 3,519,538.

When an inorganic carrier such as glass is coupled to a silane coupling agent, it is referred to as silanized. Examples of such silanized glass are alkylamine or arylalkylamine glass wherein the amine groups represent a potential organo-functional group which is linked to the silicon functional group by means of alkyl or arylalkyl groups respectively.

In the case of non-silane coupling agents, the coupling agent portion of the composites include those modified or modifiable portions of the carriers having groups or potential groups capable of chemically combining with the coenzymes. These intermediate portions may be presently available groups (e.g. aa diazotizable —$NH_2$ group) or tailor-made groups which may be subsequently modified for the coupling reactions.

The chemical coupling of NAD described in the examples below was accomplished by diazotizing the various carriers and immediately exposing the diazotized carriers to NAD to chemically couple the coenzyme by means of azo linkage. Although coupling by means of the azo linkage yields an active insolubilized product, it is thought there may be other organo-functional groups placeable on silane coupling agents or the organic carriers through which the coenzyme may be coupled without interfering with its activity. For examples of the types of organo-functional bond structures which may similarly couple the coenzyme, see U.S. Pat. No. 3,519,538.

Insolubilized composites of NAD were prepared according to the examples below. The actual coupling procedures were generally complete within about 20 minutes after contact with the threaded carriers. The coupling reaction for the NAD could be easily monitored by withdrawing aliquots of the supernatents and measuring the decreases in O.D. of the diluted samples at appropriate wavelength (e.g. 260 mu for NAD).

In view of the coupling techniques used, it was realized that a portion of the coenzyme might have been attached to the carriers by absorption rather than by covalent bonding through the coupling agents. Although absorption of the coenzyme to the carriers, which is easily accomplished, might yield products of limited value, it was a primary goal to actually chemically couple the coenzyme. Consequently, the prepared composites were treated to remove any adsorbed coenzyme. Any adsorbed coenzyme present on the composites was completely removed by thorough washing with phosphate buffer solutions. Then a representative composite (NAD coupled to glass beads) which had been subjected to the desorption treatment was used in enzymatic reactions which would yield a product only in the presence of active NAD. Thus, the determination of the product's existence, by the two methods discussed below, proved that the desorbed composite did, in fact, contain chemically coupled, active NAD.

EXAMPLE I

Porous glass particles of 40 mesh containing an average age pore diameter of 550A were used as a carrier to which NAD was coupled through a silane coupling agent. The glass particles were initially cleaned and etched by brief exposure to a concentrated HF solution and further incubation in hot 10 N NaOH for one hour. The porous glass particles were then thoroughly washed and dried.

The silane coupling agent used was alpha-aminopropyltriethoxy silane (A-1100) and it was used as obtained from Union Carbide Corporation. Both NAD and NADH (Grade III) were obtained from Sigma Chemical Company. To couple NAD to the porous glass, the following steps were taken:

A 20 gram portion of the porous glass particles was mixed with 250 ml. of dry toluene containing 10% (wt.) of the A-1100 silane and the slurry was refluxed for 24 hours. Then the porous glass was washed with toluene and acetone and dried in a vacuum oven at 60°C. The alpha-amino group was acylated by refluxing a slurry of the silanized glass particles in 250 ml. chloroform containing 10% (wt.) p-nitrobenzoyl chloride and 10% (wt.) triethylamine for 24 hours. The resulting acylated glass particles were washed thoroughly with chloroform and dried at 60°C. in a vacuum oven. The aryl nitro group was reduced to an aryl amine group by refluxing a slurry of the glass particles in 250 ml. aqueous solution of 10% (wt.) sodium dithionite for one hour.

The glass particles now containing the diazotizable coupling agent were washed with water and dried. At this stage, the glass particles can be conveniently stored since the subsequent diazotization procedure should be followed immediately by the coupling procedure to avoid deterioration of the diazo salt intermediate.

The treated glass particles were diazotized by reaction with 100 ml. of 2N HCl containing 2.5g sodium nitrite. The reaction was carried out at 0°C. in a filter flask which was continually aspirated to remove evolved $NO_2$. After 20 minutes, the reaction slurry was filtered. The diazotized glass particles were then washed with 500 ml. of cold, aqueous 1% (wt.) sulfamic acid to quench the reaction and remove traces of sodium nitrite. The particles were then immediately slurried in 50 ml. of a buffered solution (0.10 M TRIS/CHl, pH 8.5) of $10^{-2}$M NAD. The coupling reaction was carried out at room temperature. The reaction was complete in about 20 minutes and was monitored by withdrawing aliquots of the supernatent and measuring the decrease in O.D. of the diluted samples at 260 mu.

Evidence of significant coupling of NAD to the porous glass was indicated by the intense orange color of the composite. Since the composite was thought to hold both chemically coupled and adsorbed NAD, the composite was treated to remove all adsorbed NAD by thorough washing with 0.01 M, pH 8.5, phosphate buffer.

It was noted that even after the description treatment and thorough washing, very small but measurable amounts of NAD were slowly released. This was due, it is thought, to a gradual dissolution of the porous carrier at the thinner carrier sites. Since the small amounts of released NAD could have interfered with the sensitive assay techniques devised to show coupled NAD which was active (see descriptions below), it was decided to couple NAD to another glass carrier of less surface area which would not have dissolveable thin portions. In practical applications, however, it is thought the porous glass support would be a superior carrier due to its very large surface area (100 $m^2$/g) and the obvious higher concentrations of coupled NAD possible. Thus, diazotizable silanized porous glass, described above, would be a preferred carrier for the present invention.

EXAMPLE II

Solid glass beads (0.25–0.33 mm) obtained from Brownwell Scientific Company were coupled to the NAD in essentially the same manner as in Example I. Initially, however, 200g of the glass beads were used to compensate for the reduced surface area available on the glass in bead form. The glass beads were treated prior to coupling as in Example I and then coupled to the same coupling agent as in Example I. The silanized beads were then similarly diazotized and immediately coupled to NAD by slurrying the diazotized beads in 50 ml. of a buffered solution (0.10 M TRIS/HCl, pH 8.5) of $10^{-2}$M NAD. The reaction was carried out at room temperature, completed in about 20 minutes and could be monitored by withdrawing aliquots of the supernatent and measuring the decrease in O.D. of the diluted samples. Any adsorbed NAD was removed by thorough washing with 0.01 M, pH 8.5 phosphate buffer.

It was noted that the NAD-coupled glass beads had a pronounced yellow tinge instead of the intense orange color noticed in Example I. This was expected as indicating a lesser amount of coupled NAD due to the reduced surface area available on the glass beads. It was also noted that there was no detectable slow release of NAD from the glass beads and that is thought to be due to the unliklihood of measurable dissolution of the reduced area-carrier. It was decided to use this composite for later experiments to demonstrate the activity of the coupled NAD.

EXAMPLE III

NAD was coupled to several organic carriers through essentially the same diazotization procedure as in Examples I and II. To 10g of p-aminobenzylcellulose suspended in 50 ml. of 4N HCl was added 100 mg of $NaNO_2$. The temperature was maintained at 0°C. in an ice bath. The reaction was allowed to continue for 30 minutes. The product was then washed in cold distilled water and immediately added to 500mg of NAD dissolved in 0.1 M $NaCO_3$ solution. The reaction was allowed to continue overnight at 4°C. –6°C., a preferred temperature range, although the coupling procedure can be accomplished up to about room temperature successfully. Thus, the diazotization temperature may be between about 4°–20°C. The product was washed with distilled water followed by acetone and dried.

EXAMPLE IV

NAD was coupled to 10g of polyaminopolystyrene in essentially the same manner as it was coupled to the p-aminobenzylcellulose of Example III. After the same diazotization and coupling procedure, the composite was washed with distilled water followed by acetone and dried.

EXAMPLE V

Essentially the same procedures as in Examples III and IV were used to similarly couple NAD to 10g of the half amide of benzidine-carboxymethylcellulose. Again, the prepared composite was washed, dried and stored.

All of the composites prepared in the above examples can be easily treated to remove any adsorbed coenzyme by washing in a buffer solution (e.g. at pH 8.5 for coupling the NAD). The thus treated composites will then gradually contain only chemically coupled NAD.

The composite of chemically coupled NAD and glass beads, prepared according to Example II, was used in two experiments which were devised to show the coenzyme does not lose its activity in the insolubilization procedures. The methods for showing the activity of chemically coupled NAD are based on the reaction of NAD, and alcohol dehydrogenase (ADH) on the substrate ethanol to produce acetaldehyde and the reduced form of NAD (NADH). The product, acetaldehyde, can only be produced in the presence of active NAD. Thus, when the NAD insolubilized according to Example II was used in the above reaction, the generation of acetaldehyde, the existence of which is demonstrated, shows that the coupled NAD was in fact active.

In the reaction

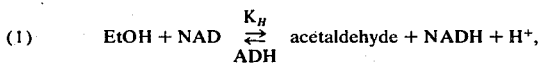

(1) $\quad EtOH + NAD \underset{ADH}{\overset{K_H}{\rightleftarrows}} acetaldehyde + NADH + H^+,$ the equilibrium can be poised in such a manner that it is sensitive to moderate pH changes. The value of $K_H$ is $1.1 \times 10^{-11}$ M. (See Richer, E. K., J. Biol. Chem. 184,313 (1950). For experimental conditions of $[EtOH] = 0.10$ M $\gg$ [NAD], [NADH], and [acetaldehyde], the equilibrium expression becomes (2) $\quad K_H[EtOH] = \dfrac{[acetaldehyde][NADH]}{[NAD]}[H^+] = 1.5 \times 10^{-12}.$ It can be calculated from equation (2) that essentially all NADH would remain reduced in a system at pH 8.5 containing catalytic quantities of ADH, 0.10 M EtOH, and $10^{-5}$M NADH for concentrations of acetaldehyde $<10^{-4}$. However, upon shifting the pH to 6.5, the equilibrium responds by converting essentially all NADH to NAD. This oxidation of NADH to NAD can be easily monitored since the differential molar extinction coefficient of NADH to NAD at 340 mu is $6.22 \times 10^3$ cm$^{-1}$. (See Kornberg et al., *Biochemical Preparations*, Vol. 3, 23, E. E. Snell, Ed., J. Wiley and Sons, N.Y. (1953). None of the other components in the above system generate sufficient absorption at a wavelength of 340 mu. Therefore, the proof of active, chemically coupled NAD was shown indirectly by first removing adsorbed NAD from the composite prepared in Example II and then using the desorbed composite of NAD with the ADH to generate acetaldehyde from ethanol at pH 8.5. Since the acetaldehyde could be generated only if the coupled NAD composite was active, the generation of acetaldehyde established that the desorbed NAD composite did in fact comprise active coupled NAD. The generation and detection of acetaldehyde was carried out according to the examples below.

EXAMPLE VI

Three ml of pH 8.5, 0.01M phosphate buffer containing 0.1M EtOH was added to a 5 ml. wet bed volume of the described NAD coupled glass beads of Example II and incubated for one hour. A one ml aliquot was removed and examined spectrophotometrically at 260 mu to ensure no free NAD had been released. Acceptable tolerances for free NAD were less than $10^{-7}$M (0.001 O.D.) which is the lower detection limit of the Cary 15 Spectrophotometer used. Appropriate control incubations with ADH and Bovine Serum Albumin (BSA), but without EtOH, did not produce any spectrophotometrically detectable release of NAD. Therefore, the results, discussed below, are not thought to be attributable to the release of or the production of soluble NAD.

The NAD coupled glass beads were then removed, washed, placed in a vial and a fresh 3 ml addition of the 0.1M EtOH buffer was added. Thirty $\mu l$ of a 1:250 dilution of yeast alcohol dehydrogenase (ADH) suspension in 0.1% BSA was used as obtained from Boehringer Mannheim Corp. and was added to the vial which was then capped. After one hour, a one ml aliquot was transfered to a 1 ml cuvette. A ten $\mu l$ portion of soluble ($10^{-3}$M) NADH was added to the cuvette and the optical density at 340 mu was recorded.

A pH jump from 8.5 to 6.5 was rapidly achieved by the addition of 6 $\mu l$ (or 6$\lambda$) of calibrated dilute HCl and 5 $\mu l$ (or 5$\lambda$) of the diluted ADH suspension was added. Then the diminishing amount of NADH, attributable to the presence of acetaldehyde, was then recorded spectrophotometrically at 340 mu.

FIG. 1 shows the $\Delta$O.D. for the NADH over a period of time after the pH drop. In effect, FIG. 1 is a spectrophotometric assay of the amount of acetaldehyde that was generated by the reaction of the insolubilized NAD and ADH with 0.10M EtOH in the 0.01M phosphate buffer at pH 8.5. The initial base line of FIG. 1 (top right) resulted from the addition of 10 $\mu l$ of the soluble ($10^{-3}$M) NADH to 1 ml of the reaction supernatent. Additional ADH (1:250 dilution of the Boehringer Suspension) was added as indicated.

The addition of the ADH requires some comment as the original ADH should be present in the reaction slurry. It has been found that additions of very dilute ADH are removed by adsorption or inactivation during a one-hour incubation period. Thus, the additional ADH was added to compensate for that loss and to allow reaction (1) to go to the left to show that acetaldehyde was in fact present. The results in FIG. 1 thus show that acetaldehyde was produced by the insolubilized NAD and ADH at pH 8.5 since the added soluble NADH could not have been gradually oxidized to NAD without the presence of acetaldehyde and active ADH after the pH drop to 6.5. It should be noted, however, that the original inactivation or adsorption of ADH was slow enough that an appreciable reaction to produce acetaldehyde took place before the ADH was no longer effectively available.

Returning to FIG. 1, it can be seen that no reaction is observed until the pH at 8.5 is jumped to 6.5 by the addition of the calibrated amount of HCl. The decrease in absorbancy (ΔO.D.) indicates at least $7 \times 10^{-6}$ acetaldehyde was present prior to the pH change. The temperature for the reaction was 25°C. and the time course of the reaction plots as a first order reaction. Considering that the NAD-glass bead bed was only about 60% of the total volume present in the vial, the effective concentration of NAD in the bed was at least $10^{-5}$M.

EXAMPLE VII

Upon refining the technique for utilizing coupled NAD, it was found possible to generate considerable quantities of acetaldehyde. Using essentially the same experimental conditions as in the acetaldehyde generation procedure of Example VI, the addition of 15 μl of the Boeringer ADH suspension, undiluted, generated so much acetaldehyde that the pH of the reaction mixture was perturbed 1.0 to 0.5 pH units lower.

Figure 2:
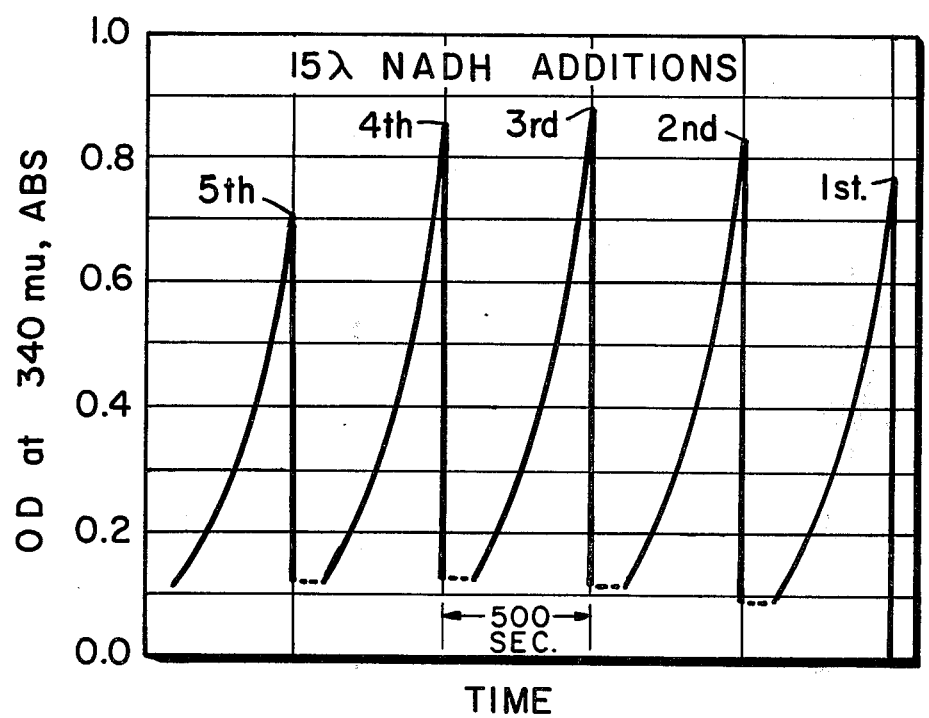
FIG. 2 shows plots of a sequential titration experiment showing a decrease of NADH which occurs in the decreasing presence of acetaldehyde at a pH of 6.5.

FIG. 2 shows the results of a sequential titration of the acetaldehyde generated in a similar experiment containing highly buffered solutions of 0.1M phosphate. In that experiment, the amount of acetaldehyde generated was sufficiently large that the equilibrium at pH 8.5 will no longer prevent the conversion of added NADH to NAD. For this reason, the pH jump from 8.5 to 6.5 was initiated before the addition of the soluble NADH. Fifteen μl additions of $8 \times 10^{-3}$M NADH were added in serial fashion to 1 ml of the supernatents containing the increased amount of acetaldehyde at pH 6.5 and the decreases in NADH were monitored at 360 mu.

The total ΔO.D. observed was 3.7, indicating $6 \times 10^{-4}$M acetaldehyde detected and the ΔO.D. was not corrected for serial dilution which would amount to only 5%. This concentration of acetaldehyde would correspond to a minimum coupled NAD concentration in the bed of about $10^{-3}$M. It should be noted that this is a minimum value for the coupled NAD concentration since the titration were not carried out to completion.

In FIG. 2, the serial spectrophotometric titrations of acetaldehyde are for acetaldehyde generated by exhaustive reaction of the insolubilized glass beads with 0.10M EtOH in 0.10M phosphate, pH 8.5. No additional ADH was added to the cuvette containing the 1 ml of the reaction supernatent since the ADH concentration was 250 fold higher than that in the experiment represented by FIG. 1. As pointed out, the pH jump from 8.5 to 6.5 was initiated prior to the additions of the soluble NADH. The various serial additions of $8 \times 10^{-3}$ NADH are indicated in FIG. 2 and represent the initial O.D. burst relative to the preceding base line. The reaction temperature was 25°C. The total, accumulated O.D. change of 3.7 represents the presence of at least $6 \times 10^{-4}$M acetaldehyde.

It was found possible to recycle the beads in NADH form back to NAD form by using 0.10M acetaldehyde at pH 6.5. Unfortunately, an essay for generated EtOH similar to that for acetaldehyde is not easily achieved due to the equilibrium perturbation by the excess aldehyde. However, NAD glass beads which have been exhaustively converted to NADH form are able to generate large quantities of acetaldehyde after the recycling reaction.

The azo linkage of NAD to the various carriers of Examples I-V is thought to be through the adenine group of the molecule. Thus, it is thought that those skilled in the art may be able to similarly insolubilize a wide variety of compounds having available adenine groups by following the teachings of this disclosure.

It should be pointed out that the carriers that can be utilized to insolubilizing the coenzymes include a wide variety of essentially insoluble materials, diverse examples of which have been described above. Also, in the examples shown, it should be noted that the only requirement for the carriers are that they be essentially water-insoluble since it is realized that even substances such as glass will tend to slowly dissolve in water. The carriers need only be diazotizable, or capable of being modified to be diazotizable, to employ the teachings of the preferred embodiment of the invention. Thus, various coupling agents, such as the described silane coupling agents, can be used to link the NAD to the carrier. The only requirement for the coupling agents is that they be capable of being modified for the coupling procedure by such methods as diazotization. Lastly, it is intended that the claimed NAD composite also include the reduced form, NADH.

I claim:

1. A method of preparing a composite consisting of nicotinamide-adenine-dinucleotide coupled chemically to a carrier material in such a manner that the nicotinamide-adenine-dinucleotide does not lose its redox properties which comprises the steps of diazotizing a carrier material selected from the group consisting of glass particles having a diazotizable silane coupling agent attached thereto, p-aminobenzylcellulose, polyaminopolystyrene, and the half amide of benzidine-carboxymethylcellulose to form a diazo salt intermediate, and immediately thereafter reacting the diazotized carrier material with an aqueous solution of nicotinamide-adenine-dinucleotide.

2. The method of claim 1 wherein the carrier material consists of porous glass particles and the silane coupling agent is alpha-aminopropyltriethoxysilane.

3. The method of claim 1 wherein the carrier material consists of glass beads and the silane coupling agent is alpha-aminopropyltriethoxy-silane.

4. The method of claim 1 wherein the diazotization temperature is between about 4° and 20°C.

5. The method of claim 1 wherein the solution of nicotinamide-adenine-dinucleotide has a concentration of $10^{-2}$ M buffered to a pH of 8.5.

6. A composite consisting of nicotinamide-adenine-dinucleotide coupled chemically to a carrier material in accordance with the method of claim 1.

* * * * *

UNITED STATES PATENT OFFICE
CERTIFICATE OF CORRECTION

PATENT NO. : 3,957,748
DATED : May 18, 1976
INVENTOR(S) : Howard H. Weetall

It is certified that error appears in the above-identified patent and that said Letters Patent are hereby corrected as shown below:

Column 3, line 8, "water-soluble" should be -- water-insoluble --.

Column 4, line 2, "if" should be -- of --.

Column 4, line 49, "threaded" should be -- treated --.

Column 5, line 52, "TRIS/CH1" should be -- TRIS/HCl --.

Column 5, line 66, "description" should be -- desorption --.

Column 7, line 16, "gradually" should be -- generally --.

Column 8, line 9, "described" should be -- desorbed --.

Signed and Sealed this

Twenty-first Day of September 1976

[SEAL]

Attest:

RUTH C. MASON
Attesting Officer

C. MARSHALL DANN
Commissioner of Patents and Trademarks